(12) United States Patent
Bebout et al.

(10) Patent No.: US 8,412,469 B1
(45) Date of Patent: Apr. 2, 2013

(54) ENVIRONMENTAL MONITORING OF MICROBE METABOLIC TRANSFORMATION

(75) Inventors: Brad Bebout, Santa Cruz, CA (US); Erich Fleming, Redwood City, CA (US); Matthew Piccini, Belmont, CA (US); Christopher Beasley, Sunnyvale, CA (US); Leslie Bebout, Santa Cruz, CA (US)

(73) Assignee: The United States of America as Represented by the Administrator of the National Aeronautics & Space Administration (NASA), Washington, DC (US)

( * ) Notice: Subject to any disclaimer, the term of this patent is extended or adjusted under 35 U.S.C. 154(b) by 317 days.

(21) Appl. No.: 12/698,996

(22) Filed: Feb. 2, 2010

(51) Int. Cl.
*G01B 3/00* (2006.01)
(52) U.S. Cl. .......................................................... 702/33
(58) Field of Classification Search ...................... 702/33
See application file for complete search history.

(56) References Cited

U.S. PATENT DOCUMENTS

2010/0005857 A1* 1/2010 Zhang et al. ................ 73/29.02

OTHER PUBLICATIONS

McCormick, et al., Algae as indicators of environmental change, Journal of Applied Phycology, 1994, 509-526, 6, Kluwer Academic Publishers, Belgium.
Campanella, et al., an Algal Biosensor for the Monitoring of Water Toxicity in Estuarine Environments, Wat. Res., Nov. 14, 2000, 69-76, 35-1, Elsevier Science Ltd, Great Britain.
Levert, et al., Modeling the growth curve for *Spirulina (Arthrospira)* maxima, a versatile microalga for producing uniformly labelled compounds with stable isotopes, Journal of Applied Phycology, 2001, 359-367, 13, Kluwer Academic Publishers, Netherlands.
Benson, et al., The development of mechanistic model to investigate the impacts of the light dynamics on algal productivity in a Hydraulically Integrated Serial Turbidostat Algal Reactor (HISTAR), ScienceDirect, Agricultural Engineering, 2007, 198-211, 36, Elsevier.
Fetscher, et al., Incorporating Bioassessment Using Freshwater *Algae* into California's Surface Water Ambient Monitoring Program (SWAMP), Technical Report prepared for California State Water Resources Control Board, May 16, 2008.
Torres, et al., Biochemical biomarkers in *algae* and marine pollution: A review, Ecotoxicology and Environmental Safety, Jul. 2, 2008, 1-15, 71, Elsevier.
Water Monitoring, Monitoring Standard for Freshwater Blue-Green *Algae*, Aquatic Ecosystem Method AEMF008, Oct. 2008, Queensland Government Natural Resources and Water.
Coad, et al., A Telemetric Monitoring System for Estuarine Algal Bloom Management, 2009, Proceeds of the 18th NSW Coastal Conference 2009.
Omar, Perspectives on the Use of *Algae* as Biological Indicators for Monitoring and Protecting Aquatic Environments, with Special Reference to Malaysian Freshwater Ecosystems, Tropical Life Sciences Research, 2010, 51-67, 21-2.

* cited by examiner

*Primary Examiner* — Jerry Lin
(74) *Attorney, Agent, or Firm* — John F. Schipper; Robert M. Padilla; Christopher J. Menke (57) ABSTRACT

Mobile system and method for monitoring environmental parameters involved in growth or metabolic transformation of algae in a liquid. Each of one or more mobile apparati, suspended or partly or wholly submerged in the liquid, includes at least first and second environmental sensors that sense and transmit distinct first and second environmental, growth or transformation parameter values, such as liquid temperature, temperature of gas adjacent to and above the exposed surface, liquid pH, liquid salinity, liquid turbidity, $O_2$ dissolved in the liquid, $CO_2$ contained in the liquid, oxidization and reduction potential of the liquid, nutrient concentrations in the liquid, nitrate concentration in the liquid, ammonium concentration in the liquid, bicarbonate concentration in the liquid, phosphate concentration in the liquid, light intensity at the liquid surface, electrical conductivity of the liquid, and a parameter α(alga) associated with growth stage of the alga, using PAM fluorometry or other suitable parameter measurements.

31 Claims, 5 Drawing Sheets

ENVIRONMENTAL MONITORING OF MICROBE METABOLIC TRANSFORMATION

ORIGIN OF THE INVENTION

The invention described herein was made in the performance of work under a NASA contract and by an employee of the United States Government and is subject to the provisions of Section 305 of the National Aeronautics and Space Act of 1958, as amended, Public Law 85-568 (72 Stat. 435, 42 U.S.C. §2457), and may be manufactured and used by or for the Government for governmental purposes without the payment of any royalties thereon or therefore.

FIELD OF THE INVENTION

This invention relates to monitoring of a plurality of environmental and growth parameters associated with growth of algae and other members of the archaea, bacteria and/or eukarya domains (collectively referred to herein as "alga" or "algae" for convenient reference).

BACKGROUND OF THE INVENTION

Growth or environmental control or other controlled metabolic transformation of archaea, bacteria and/or eukarya domains in a liquid environment is challenging, in part because the ambient liquid allows transport of nutrients and other substances between the microbes, whether of the same species or of different species. Monitoring of the individual microbes for one, two or several changes in environmental, growth and/or metabolic transformation parameters is often required, if optimal control is desired.

Monitoring and control of a large number of environmental and growth parameters is often required in order to respond to predictable and unpredictable events that occur during growth, transformation and harvesting of algae. These activities should permit distinction between parameter values at different locations and different times in the growth and metabolic transformation processes, should permit optional prescription of vehicle trajectories, should provide for collection and prompt analysis of the measurements, and should permit use of multiple vehicles.

SUMMARY OF THE INVENTION

These needs are met by the invention, which provides a method of monitoring selected environmental and/or growth parameters for growth of algae and other archaea, bacteria and/or eukarya immersed in a liquid environment. The method includes the following processes: (1) one or more distinct organisms is provided in a liquid; (2) a mobile system that floats on and/or is submergible in the liquid is provided, the mobile mechanism comprising at least first and second environmental sensors that sense distinct first and second environmental parameter values, $pv(t;1)$ and $pv(t;2)$, respectively, that are drawn from liquid temperature, temperature of gas adjacent to and above the exposed liquid surface, liquid pH, liquid salinity, liquid turbidity, $O_2$ dissolved in the liquid, $CO_2$ contained in the liquid, oxidation/reduction potential of the liquid, nitrate concentration in the liquid, ammonium concentration in the liquid, bicarbonate concentration in the liquid, phosphate concentration in the liquid, other nutrient concentrations in the liquid, light intensity at the liquid surface and below the surface, electrical conductivity of the liquid, and a parameter $\eta(alga)$ associated with growth stage of the alga; (3) the first value $pv(t;1)$ is sensed at spaced apart first and third sensing times, $t=t1$ and $t=t3$; (4) the second value $pv(t;2)$ is sensed at a second sensing time, $t=t2$, that is intermediate between the first and third sensing times; and (5) the sensed values, $pv(t1;1)$ and $pv(t3;1)$, sensed at the first and third sensing times, and the value $pv(t2;2)$, sensed at the second sensing time, are transmitted to a receiver that is spaced apart from the mobile system. Pulse amplitude modulation (PAM) fluorometry or another suitable mechanism is applied for some of these measurements.

Where a plurality of mobile systems are provided, the sensed values of a selected parameter at different locations are optionally combined with each other and a function, dependent upon location and time and representing a field of values of this parameter within or adjacent to the growth medium, is constructed for one or more sampling times and optionally displayed for a user. Optionally, this field of values is analyzed to estimate relevant environmental and/or growth parameter values and trends, to compare at least one such value with a range of acceptable values for such parameter, and to determine whether any change(s) should be introduced for such parameter.

Optionally, the mobile system is allowed to move with prevailing liquid currents in the liquid, and measurements of one or more parameter values are sampled and transmitted at each of a sequence of spaced apart times and locations, together with an estimate of the sampling location coordinates, angular orientations and corresponding sampling times. Alternatively, the mobile system is provided with a location sensing and/or angular orientation sensing mechanism and with a locomotion mechanism that is configured (i) to move the mobile system along a selected trajectory in the liquid and/or (ii) to alter or correct the mobile system present location to a selected corrected location and/or (iii) to alter or correct the mobile system present angular orientation to a selected corrected orientation.

Optionally, a time rate of change of at least one parameter value $pv(t;1)$ is estimated, based on an elapsed time difference, $\Delta t = t2 - t1$, and this elapsed time difference is adjusted subsequently according to how quickly or slowly the parameter value $pv(t;1)$ is changing with time.

Optionally, the mobile system is provided with a submersion mechanism that permits the mobile system, or a portion of the system containing at least one of the sensors, to be submerged by a selected, continuously or discretely variable depth within the liquid.

Optionally, the mobile system has a structure with at least one aperture, through which at least one sensor performs measurements of an associated environmental parameter. Optionally, measurements of two or more parameters are performed through this aperture. Optionally, at least one sample of liquid, algae or other relevant substance can be captured through this or another aperture and preserved for subsequent analysis.

On-board, or subsequent, analyses can be implemented using procedures such as PAM fluorometry of the samples to determine photosynthetic efficiency or other parameters.

Optionally, where N mobile systems are provided (N>2), a mutual repulsion system is provided for each mobile system so that any two such mobile systems that come within a selected distance of each other will repel each other, in order to prevent "bunching" or congregation of two or more such mobile systems within a small region.

The invention described in the preceding can be applied to environmental, growth and/or metabolic transformation monitoring of algae, in a liquid environment.

DESCRIPTION OF BEST MODES OF THE INVENTION

Figure 1:
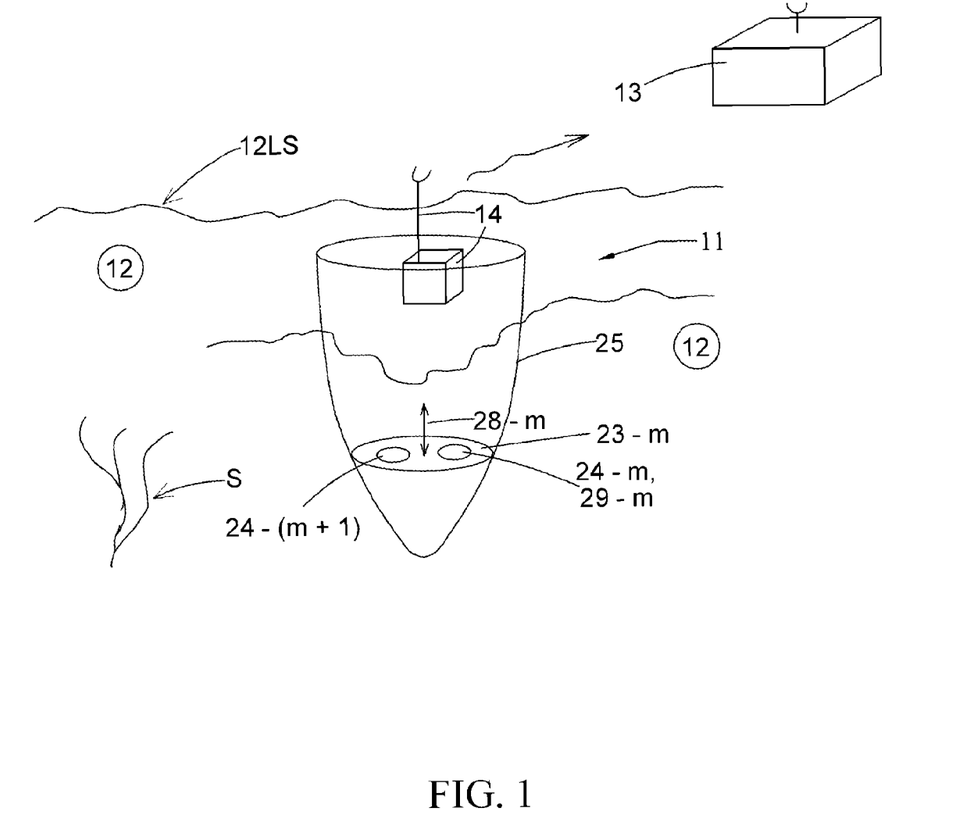
FIG. 1 illustrates use of the invention, with one mobile system, in a liquid environment.

FIG. 1 illustrates an environment where the invention can be used. A mobile system 11 floats or is submerged in a liquid 12 having a liquid surface 12LS (exposed or defined by a container surface, such as a pipe) and is intended to monitor two or more environmental, growth and/or metabolic transformation parameters (e.g., population size, population composition or metabolic activity) of the liquid or of a substance S suspended or otherwise contained in the liquid. The substance S may be one or more alga or another member of the archaea, bacteria or eukarya domains that is to be grown or otherwise transformed over a time interval. Two or more environmental and/or growth and/or metabolic transformation parameters of the substance S are to be monitored by the mobile system, as a function of time and/or as a function of location in or adjacent to the liquid 12. These monitored parameters may include, but are not limited to, liquid temperature, temperature of gas adjacent to and above the liquid surface, liquid temperature at a selected depth below the surface, liquid pH, liquid salinity, liquid turbidity, $O_2$ dissolved in the liquid, $CO_2$ contained in the liquid, oxidization/reduction potential of the liquid, concentration of ammonia, nitrate, phosphate, carbonate or other nutrient(s) or inorganic substances in the liquid, light intensity where light enters the liquid, light intensity at one or more selected depths within the liquid, electrical conductivity of the liquid, and one or more parameters $\alpha$(alga) associated with growth stage of the alga. The mobile system 11 may float on or be partially or fully submerged in the liquid or may be located within and/or move within a pipe or other container for the liquid, or the mobile system may float on or be submerged relative to an exposed liquid surface.

A first parameter value pv(t;1) is measured at two or more spaced apart times, t=t1 and t=t2 (>t1), and a second parameter value pv(t;2) is measured at one or more third times, t=t3, with t1≦t3<t2, and the measured values are transmitted to a measured signal receiver 13 that is spaced apart from the mobile system 11, using a measured signal transmitter 14 located on the mobile system. Where M (≧2) environmental parameters are monitored, times of transmission of the M parameters may be interspersed with each other, optionally in a round robin format, so that a measured signal representing each parameter value is received at one or more spaced apart times. Optionally, one or more of the measurements may use fluorometry or a similar mechanism.

Each mobile system 11 is floatable on and/or submergible in the liquid 12 or may be located within and/or move within a pipe or other closed environment containing the liquid. The mobile system 11 optionally includes a submersion mechanism 31, indicated in more detail in FIG. 3, that permits a selected portion of (or all of) the mobile system to be submerged relative to a liquid surface 12LS to a selected, continuously variable or discretely variable depth within the liquid 12. A submergible portion of the mobile system 11 optionally includes one or more parameter value sensors 23-$m$ (FIG. 1; m=1, 2, . . . , M; M≧2) that each sense one or more relevant environmental, growth and/or metabolic transformation parameters of the liquid 12 and/or of the substance S in the liquid. The measured sensor values pv(t;m) (m=1, 2, . . . , M) are transmitted by the transmitter 14 to the receiver 13 for analysis and/or storage. Optionally, each sensor 23-$m$ is located in or adjacent to one or more apertures 24-$m$ in a containment structure 25 of the mobile system 11, through which the sensor measurement can be performed. Optionally, two or more sensors are located in or associated with measurement through a common aperture.

Optionally, each mobile system 11 has a location mechanism 61 (FIG. 6) that senses the present location coordinates (x,y,z), angular orientation ($\theta;\phi$) (optional), and present time t of a designated component of the mobile system and presents this information to the transmitter 14 for transmission to the receiver 13. Optionally, a supplementary location mechanism is provided to measure or estimate a depth d(m) of the sensor 23-$m$ below the liquid surface 12LS, for transmission to the data receiver 13.

A submersion mechanism 28-$m$, which may be but need not be the same as the mobile system submersion mechanism 31, is optionally provided for separate depth control of the sensor 23-$m$. The submersion mechanism 28-$m$ allows the mobile system 11 to vary the depth of the associated sensor 23-$m$ to facilitate sensor readings at arbitrarily selected depths d(m) within the liquid 12.

Figure 3:
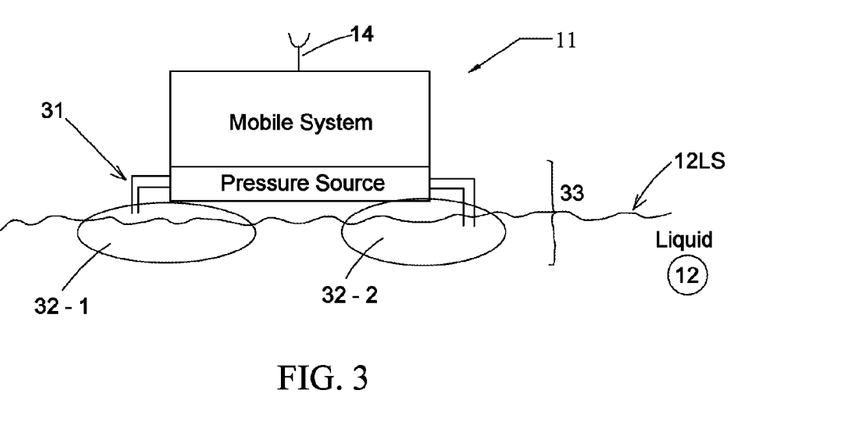

One implementation of a submersion mechanism 31 provides K inflatable bags, 32-$k$ (k=1, 2, . . . , K; K>2) or other gas enclosures at spaced apart locations on the mobile system 11, or on the sensor 23-$m$, The mass of the mobile system 11, with or without one or more selected masses attached, is assumed to be chosen so that, when each of the enclosures 32-$k$ includes a selected amount of gas (e.g., air) and has an associated baseline volume V0($k$), the mobile system and submersion mechanism 31 floats on the liquid surface 12LS of the liquid, in accord with Archimedes principle. When a selected amount of gas is released from a one, two or more of the enclosures (e.g., 32-1 and 32-2), the enclosure gas volumes are reduced to V1(1)<V0(1) and V1(2)<V0(2). As a result of this volume reduction, the mobile system 11 and/or one or more sensors 23-$m$ are (further) submerged to a controllable depth d1 below the liquid surface 12LS of the liquid, where the depth d1 depends upon the volume differences, V0(1)-V1(1) and V0(2)-V1(2).

When the mobile system 11 and/or a sensor 23-$m$ are to be brought closer to the liquid surface 12LS so that the depth d of submersion is reduced to d2<d1, gas from a re-pressurization mechanism 33 is (re)admitted into one or more of the enclosures 32-$k$ (not necessarily the enclosures, 32-1 and 32-2, that were originally partly deflated), with corresponding increases in the enclosure volumes, and the mobile system 11 and/or the sensor 23-$m$ rise to a new selected depth d2 (<d1). Appendix A contains an analysis of the dependencies of submersion depth d on enclosure volume differences.

Optionally, one or more of the sensors 23-$m$ is located adjacent to, or within, an optically or electromagnetically transparent aperture 29-$m$, through which the sensor 23-$m$ can measure or otherwise sense the environmental parameter(s) pv(t;m) associated with this sensor. Each parameter value measured or sensed by the sensor 23-$m$ is presented to the transmitter 14, for possible transmission to the data receiver 13, together with a time t(meas) at which the parameter was measured or otherwise sensed. Optionally, the measured or sensed parameter value and associated measurement time pv(tmeas;m);t(meas;m)) are transmitted to the data receiver 13 only if (1) a measurement time difference satisfies $$t2(\text{meas}); m - t1(\text{meas}; m) \geq \text{a threshold time difference} \\ \Delta t(thr; m), \quad (1)$$

which may depend upon m and/or (2) a parameter value difference satisfies $$|pv(t2;m) - pv(t1;m)| \geq \text{a threshold pv difference } pv(thr; m), \quad (2)$$

which may also depend upon m.

Preferably, the parameter value and time value signals pv(t-meas;m),t(neas;m)) are transmitted using a low power, low data rate protocol, such as Zigbee, whose protocols are partly specified by I.E.E.E. 802.15.4 standard. Zigbee uses radio frequency signals and allows relatively long battery life and secure networking. Zigbee operates in the industrial, scientific and medical (ISM) radio bands, circa 868 MHz in Europe, circa 915 MHz in the U.S. and Australia, and circa 2.4 GHz in most jurisdictions throughout the world. Zigbee can be activated in 15 msec or less so that an transmission of a isolated signal, such as pv(t(meas);m), can be preceded by transmission activation and followed by transmission de-activation, if desired, with resulting low latency and low average power consumption. Typical Zigbee applications include commercial building monitoring and control, home awareness and security, home entertainment and control, industrial plant management and control, and mobile services, such as health care/monitoring and tele-assistance.

A Zigbee communication system requires a Zigbee coordinator, one or more Zigbee routers (optional here) for forwarding data to other devices, and a Zigbee (non-forwarding) end device. The network can form a single cluster for a single mobile system 11, or a mesh of clusters (useful for a plurality of mobile systems 11). Beacon-enabled networks and non-beacon-enabled networks (number of beacons $\leq 15$) are supported. In a non-beacon-enabled network, a non-slotted code division multiple access/collision avoidance (CDMA/CA) channel access mechanism is used. A beacon-enabled network provides wakeup/transmit/sleep time intervals that are, in one version, multiples of 15.36 msec for transmission rates of 250 kbits/sec, to multiples of 24 msec for 40 kbits/sec, to multiples of 48 msec for 20 kbits/sec. The I.E.E.E. 802.15.4 standard specifies the physical layer and the media access control layer. Message acknowledgments, when used, do not rely upon CDMA/CA.

Zigbee routers, if any are used, are typically continuously active so that a robust power supply is required. The receiver (typically located on-shore and non-portable) can be configured to receive continuously, with the aid of a large(r) battery or power supply. The individual mobile systems can transmit in a slotted format, with each of M mobile systems typically being allotted a slot of length $\Delta t(\text{mob}) \approx 200$ msec in a round robin cycle of length several sec. Not all environmental parameter values pv(t';m) need be transmitted within each time slot. Optionally, only the parameter values pv(t;m) that have changed significantly since the preceding slot for the given mobile system will be transmitted within the present time slot, as indicated in Eq. (2).

Figure 4:
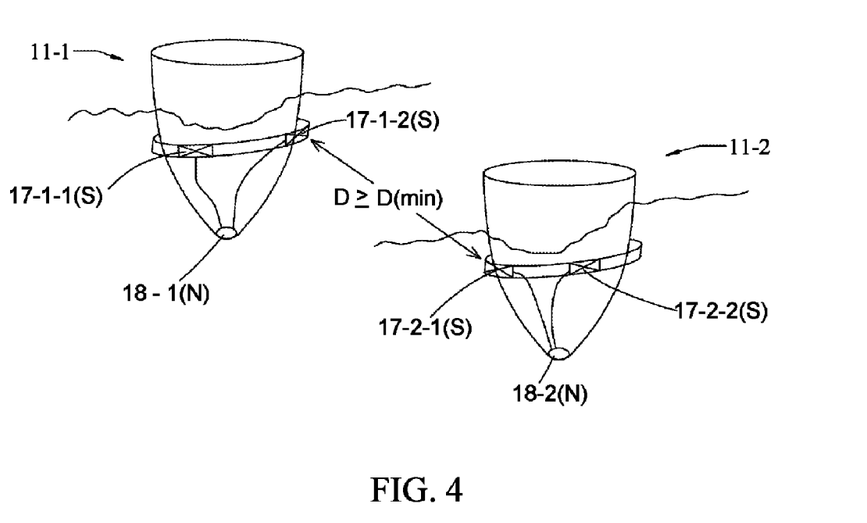
FIG. 4 illustrates a mutual repulsion system for two or more mobile systems.

Optionally, the housing for the mobile system also includes one or more sampling apertures 30-$q$ ($q=1, \ldots, Q$; $Q \geq 1$) that facilitate physical capture of one or more samples of the underwater environment (e.g., a sample of the liquid, of an alga, or of surface material in which the alga is grown). The sample, after capture, is deposited in and stored in a sample repository within the mobile system, for subsequent analysis.

Where two or more mobile systems, denoted 11-1 and 11-2 here (FIG. 4) are present, one concern is keeping the mobile systems spaced apart from each other by a distance D that is at least a minimum distance D(min) For small but positive values of D(min), for example, D(min)=1-5 cm, each mobile system is provided with at least three, preferably at least five, mutual repulsion mechanisms, 17-$j$-$k$ ($j=1, 2$; $k=1, 2, 3$) mounted on each such system that provide mutual repulsion, mobile system to mobile system. One implementation of the mutual repulsion mechanisms 17-$j$-$k$ provides three or more magnetic poles, all south poles or all north poles so that any two poles, one on mobile system 11-1 and one on mobile system 11-2, will repel each other. The three south poles 17-1-$k$ on the mobile system 11-1 (and, similarly, the three south poles 17-2-$k$ on the mobile system 11-2) are preferably connected to a single north pole 18-$j$ of an opposite magnetic sign, which is optionally located in a region elsewhere within the mobile system, as illustrated in FIG. 4. Choice of the magnetic strength of the pole 18-$j$ will strongly influence s distance of closest approach of two mutually repulsive magnets (both south poles or both north poles), one located on each of the two mobile systems. By spacing P south poles on a perimeter at approximately uniform angle differences (e.g., at $\Delta\phi \approx 360°/P$ for P such poles), the mutual repulsion of like poles will be approximately equally effective, for approach of a first mobile system to a second mobile system from any direction.

Figure 6:
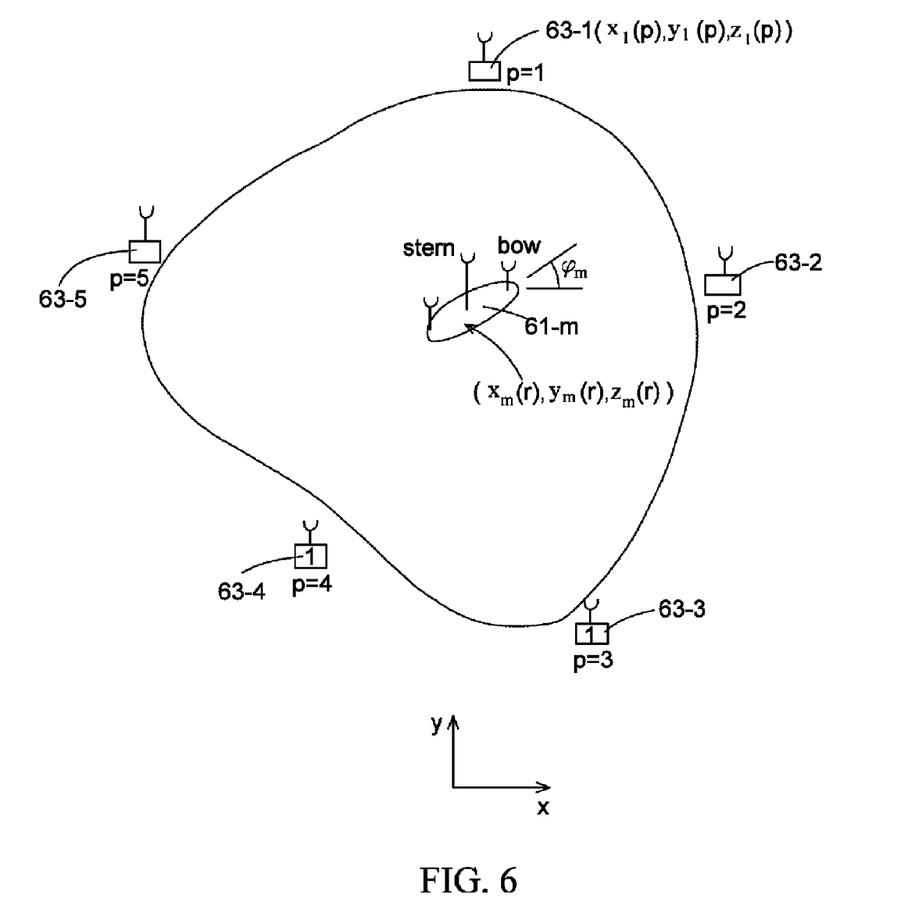
FIG. 6 illustrates estimation of location/angular orientation coordinates.

Estimation of location coordinates, angular orientation coordinates and corresponding sampling times $(x,y,z;\theta;\phi;t)$ can be implemented using GPS signals, for a relatively large body LB of liquid, or may be implemented using three or more pseudolite signal generators, located at spaced apart positions adjacent to the boundary LB, as discussed in detail in Appendix B.

Appendix A. Mechanism For Control of Submersion Depth.

Consider first and second bags or other enclosures 32-1 and 32-2 (FIG. 3) that is inflatable with a selected gas, preferably having a very low density relative to the density of the liquid 12. The enclosures, 32-1 and 32-2, are attached to a mobile system 11 and are attached to a controllable, pressurized source 33 of the selected gas, which can be introduced into one or both of enclosures or can be withdrawn from one or both of enclosures.

Figure 2:
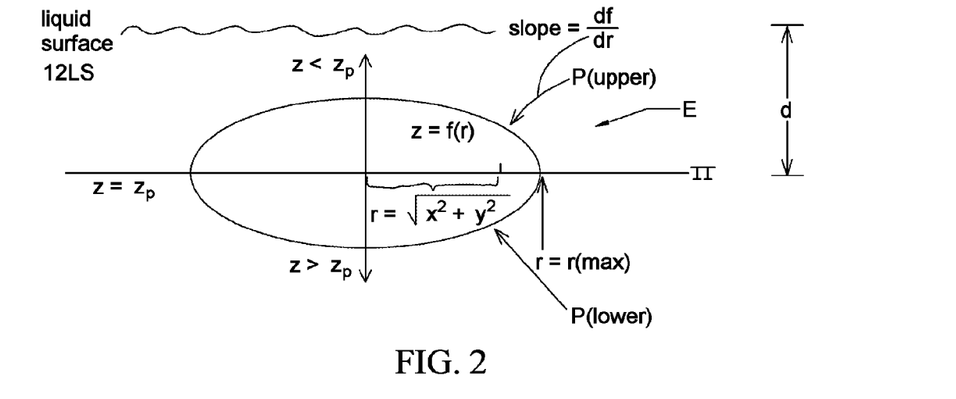
FIGS. 2 and 3 illustrate an embodiment of a submersion and flotation mechanism used in the invention.

FIG. 2 illustrates a cross section of a bag or other enclosure E, which is assumed to be symmetric about a horizontal plane $\Pi$ (referenced as a coordinate value, $z=-z_P$) and is assumed to be (approximately) rotationally symmetric about a z-axis ($x=y=0$). A cross section of the lower and upper sections of the enclosure shown in FIG. 2 are assumed to be defined as $$z = -z_P \pm f(r), \quad (A\text{-}1)$$

$$r = \sqrt{(x^2 + y^2)}, \quad (A\text{-}2)$$

where r is a radius measured in the horizontal plane $\Pi$. The function f(r) is assumed to be continuously differentiable so that the derivative or slope df/dr is defined and continuous for $0 \leq r \leq r(\max)$ (edge of the enclosure in the plane $\Pi$). Note that the corresponding slopes $\{df/dr\}$ (upper) and $\{df/dr\}$ (lower) on the upper section ($z > -z_P$) and on the lower section ($z < -z_P$) of the enclosure are related by $$\{df/dr\}(\text{upper}) = -\{df/dr\}(\text{lower}). \quad \{A\text{-}3\}$$

The total liquid force on the enclosure, assumed to be directed normal to the enclosure surface at each point, is given by $$F(z_P) = \rho 0 g \int_0^{r(\max)} \{\{[z_P - f(r)](df/dr)(\text{upper}) + [z_P + f(r)](df/dr)(\text{lower})\} 2\pi r \, dr / \{1 + (df/dr)^2\}^{1/2}, = \\ \rho 0 g \int_0^{r(\max)} \{2z_P\}(df/dr)(\text{upper}) 2\pi r \, dr, \quad (A\text{-}4)$$

$$\sin \psi = (df/dr) / \{1 + (df/dr)^2\}^{1/2}. \quad (A\text{-}5)$$

where it is assumed that the horizontal plane Π is located at a depth $\Delta z = z_P$ below the surface of the liquid 12, and that the mass or pressure equivalent of this liquid (per unit depth below the liquid surface) is ρ0 (e.g., 62.4 lbs. per cubic foot for water as the liquid 12), A corresponding volume of the enclosure interior is $$V = \int_0^{r(max)} 2f(r) 2\pi r \, dr. \tag{A-6}$$

The total liquid force F is directed upward, toward negative values of the coordinate z. Note that, for any smooth shape f(r) of the enclosure cross section, the total liquid force F on the enclosure is proportional to the depth parameter $z_P$ and is usually directed upward. Equation of the force F and the mobile system weight w(mobile) will provide an equilibrium depth $z_P$ at which the (submerged) enclosure plus weight will settle. As the amount of the selected gas introduced into the enclosure E increases, the shape function f(r) changes, the volume within the enclosure increases, and the equilibrium value of the depth parameter $z_P$ decreases so that the mobile system 11 rises in the liquid; and conversely. The net energy required to cause the depth parameter $z_P$ to decrease by a controllable amount so that the mobile system 11 rises in the liquid is substantially equal to the energy required to introduce the additional gas into the enclosure interior, which is relatively small. Optionally, when the depth parameter $z_P$ is to be increased so that the mobile system sinks by a controllable amount, a portion of the selected gas in the enclosure interior can be bled off and allowed to pass into the ambient medium, with little or no additional energy expenditure.

Assuming that the mass of an attached mobile system, including ballast masses, if desired, is m(total), the enclosure(s) E will rise in the supporting liquid to an enclosure depth $\Delta z = z_p$ for which $$F(z_P) = m(\text{total}) \cdot g. \tag{A-7}$$

This relation may be corrected, if desired, for the supplemental buoyancy for the mobile system 11 that is provided by the supporting liquid.

Appendix B. Estimation of Location Coordinates and Angular Orientation

Coordinates and Sampling Times.

Consider a mobile system 61-m (m=1, ..., M; M≧1) that is floating on or submerged in a liquid 62, having a boundary ∂B, as illustrated in FIG. 6. Three or more spaced apart pseudolites, 63-k (k=1, ..., K; K≧5) are located at selected distances from the boundary ∂B, or optionally within the liquid, each pseudolite 63-k has known and fixed coordinates $(x_k, y_k, z_k)$, and any three of the pseudolites are non-collinear. A signal receiver 62 is located at a selected position, relative to or on the mobile system 61-m. The mobile system 61-m has a timing mechanism that is coordinated with a timing mechanism on each of the pseudolites 63-k. At each of a specified sequence of spaced apart times, $\{t=t_{k,m}\}_m$, the pseudolite 63-k transmits a short location/timing signal $S_{L/T}(t_{k,m})$, preferably including a coded portion that identifies the pseudolite source and specifying the time this signal is transmitted. The signal $S_{L/T}(t_{k,m})$ is received by a receiver antenna on the mobile system 61-m, which computes a time difference $$\Delta t_{k,m} = t_{a,k,m} - t_{k,m}, \tag{B-1}$$

between a time, $t = t_{a,k,m}$, this signal is received by the receiver antenna (m) and the signal transmission time for the pseudolite (k). A separation distance, $$d_{k,m}(t) = c\Delta t_{k,m} \tag{B-2}$$
$$= \{(x_m(r) - x_k(p))^2 + (y_m(r) - y_k(p))^2 + (z_m(r) - z_k(p))^2\}^{1/2},$$

between the receiver antenna, having location coordinates $(x_m(r), y_m(r), z_m(r))$, and the pseudolite, having location coordinates $(x_k(p), y_k(p), z_k(p))$, is then estimated, where c is the propagation velocity of an electromagnetic signal in the ambient environment (the "speed of light").

Each pseudolite will have fixed location coordinates that do not vary with time, and preferably any temporal variation between the timers for each pair of pseudolites is immediately corrected, through p-to-p communication. However, an individual receiver associated with a mobile system (m) will have varying location coordinates, and the on-board timer for this mobile system may have a time shift, $\Delta t = \tau(t;m)$ that varies with time and varies with the particular mobile system (m) being examined. This time shift (positive, zero or negative; unknown initially) is explicitly incorporated in the equations for distance as follows:

$$\{(x_m(r) - x_k(p))^2 + (y_m(r) - y_k(p))^2 + (z_m(r) - z_k(p))^2\}^{1/2} = c\{\Delta t(k.m) + \tau(t;m)\}(k=1,\ldots,K; m \text{ fixed}), \tag{B-3(k,m)}$$

where $\Delta t(k,m)$ is a time difference measured at the pseudolite number k or measured at the mobile system number m. Equations (B-3(k,m)) for k=2, 3, 4, etc. (m fixed) are squared and subtracted from Eq. (3-B(k=1 μm) as follows.

$$\{(x_m(r) - x_k(p))^2 + (y_m(r) - y_k(p))^2 + (z_m(r) - z_k(p))^2\} -$$
$$\{(x_m(r) - x_1(p))^2 + (y_m(r) - y_1(p))^2 + (z_m(r) - z_1(p))^2\} =$$
$$2\{x_m(r)(x_1(p) - x_k(p)) + y_m(r)(y_1(p) - y_k(p)) + z_m(r)(z_1(p) - z_k(p))\} +$$
$$x_k(p)^2 - x_1(p)^2 + y_k(p)^2 - y_1(p)^2 + z_k(p)^2 - z_1(p)^2 +=$$
$$c^2\{\Delta t(k.m) + \tau(t;m)\}^2 - c^2\{\Delta t(1.m) + \tau(t;m)\}^2 +=$$
$$c^2\{2\tau(t;m)(\Delta t(k,m) - \Delta t(1,m)) + \Delta t(k,m)^2 - \Delta t(1,m)^2\}(B-4(k,m))$$

The unknowns here are the location coordinates, $x_m(r)$, $y_m(r)$ and $z_m(r)$, and the time shift t(t;m) for the mobile system 61-m; all other quantities are known. Equations (B-4(k,m)) can be re-expressed in matrix form as $$M \cdot X = H, \tag{B-5}$$

$$M = \begin{bmatrix} x_1(p) - x_k(p) & (y_1(p) - y_k(p) & z_1(p) - z_k(p) & \Delta t(k,m) - \Delta t(1,m) \\ x_1(p) - x_k(p) & (y_1(p) - y_k(p) & z_1(p) - z_k(p) & \Delta t(k,m) - \Delta t(1,m) \\ x_1(p) - x_k(p) & (y_1(p) - y_k(p) & z_1(p) - z_k(p) & \Delta t(k,m) - \Delta t(1,m) \\ x_1(p) - x_k(p) & (y_1(p) - y_k(p) & z_1(p) - z_k(p) & \Delta t(k,m) - \Delta t(1,m) \end{bmatrix}, \tag{B-6}$$

-continued $$X^{tr} = [x_m(r) y_m(r) \ z_m(r) \ \tau(t; m)], \quad (B-7)$$

$$2H^{tr} = [x_1(p)^2 - x_k(p)^2 + y_1(p)^2 -$$
$$y_k(+z_1(p)^2 - z_k(p)^2 + c^2(\Delta t(k, m)^2 - \Delta t(l, m)^2), x_1(p)^2 -$$
$$x_k(p)^2 + y_1(p)^2 - y_k(+z_1(p)^2 - z_k(p)^2 +$$
$$c^2(\Delta t(k, m)^2 - \Delta t(l, m)^2), x_1(p)^2 - x_k(p)^2 + y_1(p)^2 -$$
$$y_k(+z_1(p)^2 - z_k(p)^2 + c^2(\Delta t(k, m)^2 - \Delta t(l, m)^2),$$
$$x_1(p)^2 - x_1(p)^2 + y_1(p)^2 -$$
$$y_k(+z_1(p)^2 - z_k(p)^2 + c^2(\Delta t(k, m)^2 - \Delta t(l, m)^2)]$$

The matrix M has an inverse $M^{-1}$ (rank 4), in part because no three of the location coordinate triples $(x_i(p), y_i(p), z_i(p))$ (i=1, 2, 3, 4, 5) for the pseudolites are collinear. The matrix solution X of Eq. (B-5) becomes $$X = M^{-1} H. \quad (B-9)$$

The time shift $\tau(t;m)$ for mobile system 61-$m$ may, but need not, vary with time t.

The location coordinates $(x_m(t;r), y_m(t;r), z_m(t;r))$ estimated for mobile system 61-$m$ will vary with time t as the mobile system moves on or within the liquid 62. Two consecutive sampling times, $t_n$ and $t_{n+1}$, for the mobile system 61-$m$ may be determined by identifying a time difference, $t_{n+1} - t_n$, for which a separation distance first satisfies $$\{(x_m(t_{n+1};r) - x_m(t_n;r))^2 + (y_m(t_{n+1};r) - y_m(t_n;r))^2 + (z_m(t_{n+1};r) - z_m(t_n;r))^2\}^{1/2} \geq d(thr), \quad (B-10)$$

where $d(thr)$ is a selected threshold separation distance, which is chosen according to an estimated difference in one or more environmental parameters that may occur with the separation distance $d(thr)$. This sampling frequency may vary from one environmental parameter to another.

Angular orientation coordinates $(\phi, \theta) = $ (azimuthal angle, polar angle) for the mobile system, relative to a horizontal plane may be estimated by obtaining the location coordinates, $(x_m(r;\text{bow}), y_m(r;\text{bow}), z_m(r;\text{bow}))$ and $(x_m(r;\text{stern}), y_m(r;\text{stern}), z_m(r;\text{stern}))$ for spaced apart, first and second locations on the bow and on the stern, respectively, of the mobile system 61-$m$. These location coordinates may be estimated, applying the considerations involved in Eqs. (B-1) through (B-9) to measurements made at a second data receiver located on the bow and at a third data receiver located on the stern of the mobile system 61-$m$. The angles $\phi_m$ and $\theta_m$ for mobile system no. m are then estimated from the relations $$\tan\phi_m = \{y_m(r; \text{bow}) - y_m(r; \text{stern})\}/\{x_m(r; \text{bow}) - x_m(r; \text{stern})\}, \quad (B-11)$$

$$\tan\theta_m = \{z_m(r; \text{bow}) - z_m(r; \text{stern})\}/\{x_m(r; \text{bow}) - x_m(r; \text{stern}))^2 + (y_m(r; \text{bow}) - y_m(r; \text{stern}))^2\}^{1/2}, \quad (B-12)$$

Normally, the polar angle $\theta_m$ will be close to 0, because the mobile system will be approximately horizontal in the liquid 62.

Appendix C. Construction of a Surface From a Field of Values.

Figure 5:
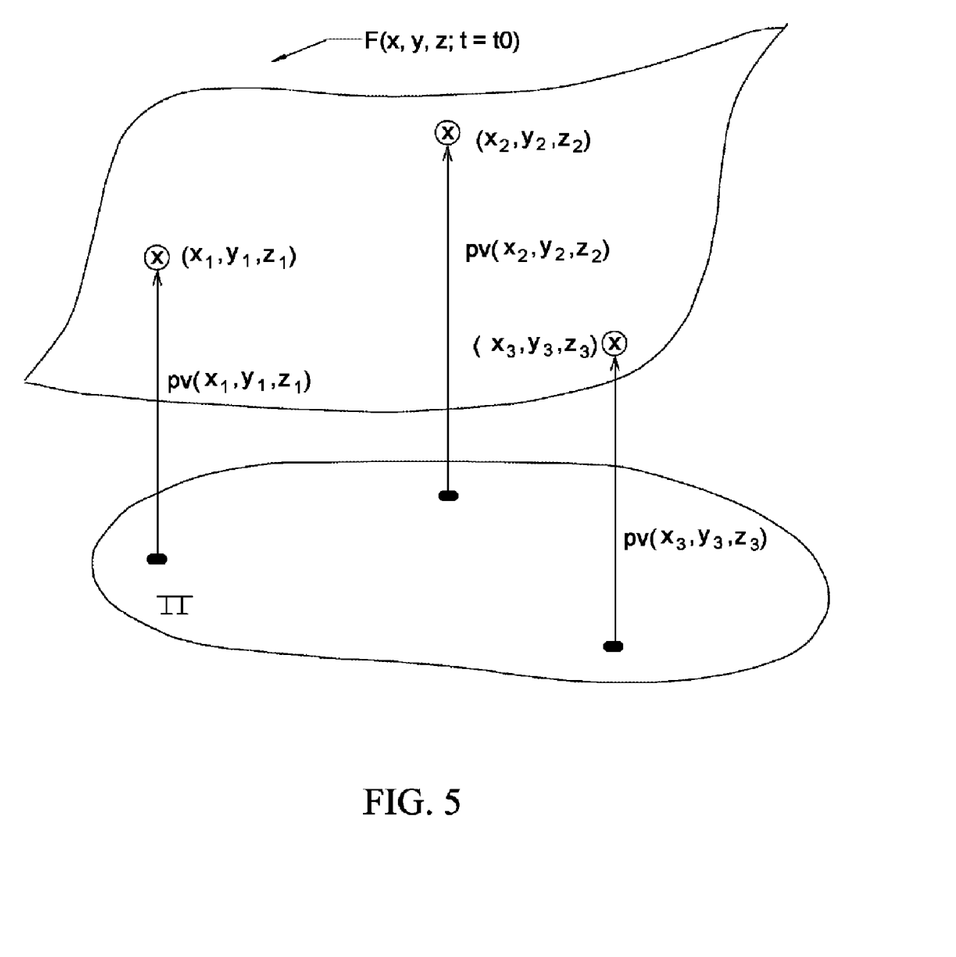
FIG. 5 illustrates construction of a field of values determined according to the invention.

Consider a field of measured values $pv(x_k, y_k, z_k, t_k; m)$ (k=1, ..., K) of a selected environmental parameter (m fixed), where the values have been measured at times ($t_k \approx t0$, a time value independent of k) that are reasonably close to each other. This is preferably done using two or more mobile systems, which may be individually stationary or may move relative to each other. If the integer K is not too large (preferably, $K \leq 20$, and more preferably $K \leq 10$), a three-dimensional field or surface of values that precisely matches the values $pv(x_k, y_k, z_k, t_k; m)$ for the coordinates $(x=x_k, y=y_k, z=z_k)$ is constructed, as illustrated in FIG. 5. This field of values is defined by $$F(x, y, z; t \approx t0) \sum_{k=1}^{K} pv(x_k, y_k, z_k, t_k; m) \prod_{j=1, j \neq k}^{K} \{(x - x_j)(y - y_j)(z - z_j)/(x_k - x_j)(y_k - y_j)(z_k - z_j)\}, \quad (C-1)$$

$$F(x_k, y_k, z_k, ; t \approx t0) = pv(x_k, y_k, z_k, t_k; m), \quad (C-2)$$

where, for each value k, the finite product Π is formed for all ratios $(x - x_j)/(x_k - x_j)$ for which $j \neq k$. The function F is a polynomial of degree K in each of the coordinates x, y and z and is representable as a surface S of height $pv(x_k, y_k, z_k, t_k; m)$ above a plane Π at the location $(x_k, y_k, z_k)$, as illustrated in FIG. 5.

Where two or more measurement locations $(x_k, y_k, z_k)$ have at least one of the same coordinate values, $x_k$ or $y_k$ or $z_k$, a new "rotated plane" with coordinates (x',y',z') is introduced, defined by $$\begin{bmatrix} x \\ y \\ z \end{bmatrix} = M_2(\beta) \cdot M_3(\alpha) \begin{bmatrix} x' \\ y' \\ z' \end{bmatrix} \quad (C-3)$$

$$M_3(\alpha) = \begin{bmatrix} \cos\alpha & \sin\alpha & 0 \\ -\sin\alpha & \cos\alpha & 0 \\ 0 & 0 & 1 \end{bmatrix} \quad (C-4)$$

$$M_2(\beta) = \begin{bmatrix} \cos\beta & 0 & \sin\beta \\ 0 & 1 & 0 \\ -\sin\beta & 0 & \cos\beta \end{bmatrix} \quad (C-5)$$

The angular variables $\alpha$ and $\beta$ are chosen so that an equivalent finite product $$F'(x', y', z'; t \approx t0) \sum_{k=1}^{K} pv(x'_k, y'_k, z'_k, t_k; m) \prod_{j=1, j \neq k}^{K} \{(x' - x'_j)(y' - y'_j)(z' - z'_j)/(x'_k - x'_j)(y'_k - y'_k)z_j - z'_k)\}, \quad (C-6)$$

expressed in terms of the equivalent coordinates (x',y',z'), does not include any situation in which $x'_j = x'_k$ or $y'_j = y'_k$ or $z'_j = z'_k$. This can be achieved in a straightforward manner, because the total number of coordinates $(x_j, y_j, z_j)$ is finite and equal to 3K. The coordinates (x',y',z') are then expressed in terms of the original coordinates (x,y,z) as $$\begin{bmatrix} x' \\ y' \\ z' \end{bmatrix} = M_3(-\alpha) \cdot M_2(-\beta) \begin{bmatrix} x \\ y \\ z \end{bmatrix} \quad (C-7)$$

which is the inverse of Eq. (C-3). The resulting field of values function F"(x,y,z;t≈t0) will be a polynomial with the same maximum degree (K) in each of the coordinates but may not be expressible in the elegant form set forth in Eq. (C-1). In order to avoid high polynomial degrees, with the associated frequency variation in each of the location coordinates, it is preferable to limit the number K of sampled pv values to a relatively small integer, such as K=3-6.

It is important to control certain environmental parameters to insure that these parameters stay within a suitable range in order to avoid adversely interfering with the growth or metabolic transformation process for a particular microbe. These parameters include: liquid pH (preferred range=$3.5 \leq pH$(liq)$\leq 9.5$); liquid temperature T ($0°$ C.$\leq T$(liq)$\leq 40°$ C.); $CO_2$ concentration (0-10 mmoles/liter); $O_2$ concentration (0-1 mmole/liter); nutrient concentration (0-1 mmole/liter); light irradiance I adjacent to a liquid surface (0-2500 photons/(meter)-2-sec).

Appendix D. Application of Fluorometry to Transformation Measurements.

In a fluorescence process, incident light having energy $E=h\nu=hc/\lambda$ is absorbed by an object, a portion of the light energy is transformed into one or more other processes, and the remainder, if any, is re-emitted at a higher wavelength, $\lambda'>\lambda$ or $\nu'<\nu$, representing a lower emission energy. The remainder of the incident energy may be absorbed and used for photosynthesis, for heat dissipation and/or for quantum processes such as (temporary) atomic or molecular excitation. This perspective may be expressed as an equation $$E = h\nu + \text{photosynthesil}(E_{ps}) + \text{heat dissipation}(E_{diss}) + \text{quantum processes}(E_{qp}) + \text{fluorescence}(E_{FL} = h\nu') \quad (D-1)$$

For simplicity, the presence of quantum processes is ignored here.

When a leaf or other biological object is kept in the dark, with no energy supplied, the characteristic internal energy of the object will decrease toward a minimum energy value $E_{min}$. When this object is illuminated with incident light ($E=h\nu$), the reissued fluorescence signal energy $E_{FL}$ will increase to a maximum value $E_{max}$, with the remainder, $E_{ps}+E_{diss}$, being generally not observable optically. The difference, $E_\nu = E_{max}-E_{min}$, is referred to as the variable fluorescence and has a range of values, $E_\nu \approx 0.8\ E_{max}$, for healthy, growing plants. For many algae, the ratio $E_\nu/E_{max}$ has an optimal range, depending upon the process of interest., and the system approaches this optimal range monotonically as growth or other metabolic transformation proceeds.

When non-saturating light is received by a target (e.g., chlorophyll a), the target is elevated to an excited state in which an electron is transferred into an electron transport chain (ETC), which can be subsequently used for other purposes, such as production of ATP, reduction of NADP, and production of glucose. After electron transfer to and through an ETC has occurred, the electron acceptor becomes available again to accept another electron. When higher light intensity is delivered, the reaction centers become temporarily inactivated (closed) until electrons presently in the reaction centers are cleared out through transfer. When this saturation and temporary closure occurs, excess incident light is re-emitted as fluorescence, which can be measured and used as a diagnostic parameter to estimate the present status of the target. When a group of cells is under stress, saturation occurs more easily, and the system processes the incident light less efficiently than would occur in a group of cells not under such stress.

A fluorescence target is initially kept in the dark, to allow the ETC to become cleared of electrons and to open all acceptor channels. At this point, the system is most efficient in accepting small amounts of incident light and in processing the electrons produced in the excited states. As the system approaches saturation, efficiency decreases. System efficiency changes more quickly when system stress is present and saturation occurs at reduced (time-integrated) incident light levels.

Photo-excitation of the fluorescence target is preferably implemented using pulse light, with an excitation interval having a temporal length in a range of 0.1 μsec-1 msec, in order to avoid saturating the target and to estimate the minimum value $E_{min}$. Delivery of a single, longer pulse, with an associated time interval length in a range 0.1-2 sec can be used to estimate a fluorescence saturation energy level.

A pulse amplitude modulation (PAM) fluorometer can deliver incident light pulses in one or several different wavelength ranges ($\lambda$) and at different light delivery rates $r(\lambda)$, in order to estimate the efficiency parameter $F_\nu/F_M$ (comparable to $E_\nu/E_{max}$) and an initial value $E_{min}$. The fluorescence efficiency will vary with the wavelength range used and with the light delivery rate. A PAM fluorometer uses three or four wavelength ranges to estimate the presence and concentrations of at least three groups of algae: (i) green algae (sensed by presence of chlorophyll b); (ii) cyanobacteria (sensed by presence of allophycocyanin), and (iii) diatom/dinoflagellate (sensed by presence of chlorophyll c, fucoxanthin and carotenoids). Other wavelength-related groups can also be used here. Stress of a group of cells in the target can be implemented through $O_2$ deprivation, $CO_2$ deprivation, nitrate (salt) excess or deficit, or other nutrient excess or deficit, among others.

PAM fluorometry allows control of at least four parameters for monitoring a present stage of micro-organism and selected environmental parameters: wavelength range, light intensity or irradiance, duration of exposure, and duty cycle (fraction of time the micro-organism is exposed to light).

What is claimed is:

1. A method of monitoring an environment for growth or transformation of algae, the method comprising:
   providing at least one alga, immersed in, or adjacent to a surface of, a liquid;
   providing a mobile system that floats on and is submersible in the liquid to a controllable depth, the mobile mechanism comprising at least first and second environmental sensors that sense distinct first and second environmental parameter values, pv(t;1) and pv(t;2), respectively, where at least one of the first and second environmental sensors senses at least one of liquid temperature at a selected depth within the liquid, temperature of gas adjacent to and above the liquid, liquid pH, liquid salinity, liquid turbidity, $O_2$ dissolved in the liquid, $CO_2$ concentration in the liquid, oxidization and reduction potential of the liquid, nitrate concentration in the liquid, ammonium concentration in the liquid, bicarbonate concentration in the liquid, phosphate concentration in the liquid, light intensity where light enters the liquid, electrical conductivity of the liquid, and an alga parameter that is a measure of growth stage of the alga, and another of the at least two environmental sensors senses light intensity at a selected depth in the liquid;
   sensing the first environmental parameter value pv(t;1) at spaced apart first and third sensing times, t=t1 and t=t3;
   sensing the second environmental parameter value pv(t;2) at a second sensing time, t=t2, that is intermediate between the first and third sensing times; and
   transmitting the environmental parameter values, pv(t=t1;1) and pv(t=t3;1), sensed at the first and third sensing times, and the environmental parameter value pv(t=t2;2), sensed at the second sensing time, to a data receiver.

2. The method of claim 1, further comprising providing a locomotion mechanism that is configured to move said mobile system along a selected trajectory in said liquid.

3. The method of claim 1, further comprising providing a location sensing mechanism that provides at least first and second sets of location observation coordinates of said mobile system for at least first and second location observation times, respectively, and transmits the at least first and second sets of location observation coordinates and the at least first and second location observation times to said data receiver.

4. The method of claim 3, wherein said location sensing mechanism provides said at least first and second sets of said location observation coordinates of said mobile system by a procedure comprising:
transmitting timed electromagnetic signals from at least first, second and third electromagnetic signal sources, spaced apart from each other and from said mobile system, at determinable first, second and third location signal emission times, respectively, to a location signal receiver on said mobile system; and
estimating at least first and second location coordinates (x,y) for a first mobile system location, determined with reference to the location signal receiver at a location signal receipt time, determined with reference to at least one of the first, second and third location signal emission times.

5. The method of claim 3, wherein said location sensing mechanism provides at least one of two angular orientation coordinates, $\theta$ and $\phi$, for said mobile system by a procedure comprising:
transmitting timed electromagnetic signals from at least first, second and third spaced apart electromagnetic signal sources at determinable first, second and third location signal emission times at a first and second, spaced apart location signal receivers located on said mobile system;
estimating at least first and second location coordinates $(x_k, y_k)$ for each of first and second spaced apart locations, corresponding to k=1 and k=2, respectively, on said mobile system, determined with reference to the first location signal receiver and the second location signal receiver, respectively, at a location signal receipt time, determined with reference to at least one of the first, second and third location signal emission times; and
determining at least one of the angular orientation coordinates, $\theta$ and $\phi$, for said mobile system with reference to an angular orientation of a line segment extending between first and second locations having the respective location coordinates $(x_1, y_1)$ and $(x_2, y_2)$.

6. The method of claim 3, further comprising:
providing a locomotion mechanism that is configured to move said mobile system along a selected mobile system trajectory in said liquid;
representing the mobile system trajectory as a sequence of trajectory location coordinates representing at least first and second spaced apart locations, through which the mobile system trajectory passes, and corresponding first and second location observation times;
receiving the location observation coordinates at a location signal receiver and providing observation location coordinates for the at least first and second location observation times;
comparing the location observation coordinates with the mobile system trajectory location coordinates for the at least first and second locations through which the mobile system trajectory passes; and
when a distance between the location observation coordinates and the mobile system trajectory location coordinates, for at least one of the first and second locations through which the mobile system trajectory passes, is greater than a selected threshold distance, issuing a correction signal to vary at least one location observation coordinate of the mobile system relative to the mobile system trajectory.

7. The method of claim 1, wherein said mobile system is permitted to move in said liquid according to prevailing liquid currents in said liquid.

8. The method of claim 1, further comprising:
providing an elapsed time difference value between said first sensing time and said second sensing time for said first sensed parameter value;
providing an estimation of a time rate of change of said first sensed parameter value; and
adjusting the elapsed time difference so that this difference decreases monotonically with increase in the time rate of change of said first sensed parameter value.

9. The method of claim 8, further comprising adjusting said elapsed time difference so that a change in said first sensed parameter value, between at least two consecutive sensing times, does not exceed a selected fraction f of an average value of said first sensed parameter value, where f lies in a range 0<f<1.

10. The method of claim 9, further comprising selecting said fraction f in a range of 0.01 to 0.20.

11. The method of claim 1, wherein said first sensed parameter value pv(t;1) and said second sensed parameter value pv(t;2) are transmitted with respective first and second parameter value reporting frequencies that are different from each other.

12. The method of claim 1, wherein said first sensed parameter value pv(t;1) and said second sensed parameter value pv(t;2) are transmitted with respective first and second parameter value reporting frequencies that are the same.

13. The method of claim 1, further comprising:
receiving at least 2K+1 first sensed parameter values in a selected time interval, where K is a selected positive integer;
forming a weighted average WA1 of the at least 2K+1 received first sensed parameter values; and
replacing each of the at least 2K+1 first sensed parameter values by the weighted average AW1.

14. The method of claim 1, further comprising:
receiving a sequence of at least 2K+1 first sensed parameter values in a selected time interval, where K is a selected positive integer; and
selecting a first sensed parameter value that is a median of the sequence.

15. The method of claim 1, further comprising:
receiving at least 2K+1 first sensed parameter values in a selected time interval, where K is a selected positive integer;
arranging the at least 2K+1 first sensed parameter values in a sequence that is monotonically increasing or monotonically decreasing; and
choosing a first sensed parameter value that represents at least one of a majority view choice and a plurality view choice among the sequence.

16. The method of claim 3, further comprising providing a submersion mechanism, attached to said mobile system, that permits said mobile system to be submerged or raised to a selected and continuously variable or discretely variable depth.

17. The method of claim 16, wherein said mobile system is submerged within said liquid by a procedure comprising:
  providing at least first and second bags that are inflatable with a selected gas and that are attached at spaced apart locations on said mobile system, where the first and second bags contain first and second selected amounts, respectively, of first and second selected gases;
  when said mobile system is to be raised to said selected depth within said liquid, increasing the selected amount of the selected gas in at least one of the first and second bags; and
  when said mobile system is to be lowered to said selected depth within said liquid, decreasing the selected amount of the selected gas in at least one of the first and second bags.

18. The method of claim 1, further comprising providing said mobile system with an external covering having at least one aperture through which an adjacent portion of said liquid is exposed to sense at least one of said first and second environmental parameters so that at least one of said environmental parameter values can be measured in said liquid.

19. The method of claim 18, wherein at least two of said at least first and second environmental parameters is sensed through said at least one aperture.

20. The method of claim 18, further comprising providing a signal transmitting mechanism, having a signal transmission antenna, on an upper portion of said external covering.

21. The method of claim 18, further comprising providing said external covering with a lower portion that is shaped as a portion of a prolate spheroid that is partly or wholly submerged in said liquid.

22. The method of claim 18, further comprising providing said external covering with a lower portion that is shaped as an M-hedral surface ($M \geq 3$) that is partly or wholly submerged in said liquid.

23. The method of claim 1, further comprising:
  comparing said sensed first environmental parameter value $pv(t1;1)$ for a selected alga, sensed at said first sensing time, with a range of acceptable values $pv1(ref)$ of said first parameter value;
  when said sensed first parameter value $pv(t1;1)$ is not within the acceptable range of values $pv1(ref)$, interpreting this condition as indicating that growth of the selected alga should be discontinued.

24. The method of claim 1, further comprising:
  submerging said mobile system to a selected positive depth in said liquid, corresponding to a selected alga having selected location observation coordinates, at spaced apart location observation times, $t=t4$ and $t=t5$;
  estimating said light intensity in said liquid at the selected location observation coordinates at the location observation times, $t=t4$ and $t=t5$; and
  estimating an amount of growth of the selected alga for at least one of the times $t4$ and $t5$.

25. A method of monitoring an environment for growth or transformation of algae, the method comprising:
  providing at least one alga immersed in, or adjacent to a surface of, a liquid;
  providing N mobile systems ($N \geq 2$), numbered $n=1, \ldots, N$, where each mobile system floats and/or is submersible in the liquid to a controllable depth, and each mobile system, number n, comprises at least first and second environmental sensors that sense distinct at least first and second environmental parameter values, $pv(t;1)$ and $pv(t;2)$, respectively, in common, where at least one of the first and second environmental sensors senses at least one of liquid temperature, temperature of gas in the liquid, liquid pH, liquid salinity, liquid turbidity, $O_2$ dissolved in the liquid, $CO_2$ contained in the liquid, oxidization and reduction potential of the liquid, nitrate concentration in the liquid, ammonium concentration in the liquid, bicarbonate concentration in the liquid, phosphate concentration in the liquid, light intensity where light enters the liquid, electrical conductivity of the liquid, and an alga parameter that is a measure of growth stage of the alga, and another of the at least two environmental sensors senses light intensity at a selected depth in the liquid;
  sensing the first parameter value $pv(t;1;n)$ at spaced apart first and third sensing times, $t=t1$ and $t=t3$, for each of the N mobile systems to provide sensed first parameter values, $pv(t1;1;n)$ and $pv(t3;2;n)$ for the mobile system number n;
  sensing the second parameter value $pv(t;2;n)$ at a second sensing time, $t=t2$, which is intermediate between the first and third sensing times, to provide a sensed second parameter value $pv(t2;2;n)$ for the mobile system number n;
  transmitting the values, $pv(t1;1;n)$ and $pv(t2;2;n)$, to a data receiver that is spaced apart from at least one of the N mobile systems.

26. The method of claim 25, further comprising:
  allowing each of said N mobile systems to move with liquid currents in said liquid; and
  providing a location sensing mechanism for each of said N mobile systems that senses and provides at least first and second sets of location observation coordinates ($x_n(t), y_n(t), z_n(t)$), ($n=1, \ldots, N$) for said mobile system number n for at least first and second spaced apart location observation times, $t=t1$ and $t=t2$, respectively, and transmits the at least first and second sets of location observation coordinates, and the at least first and second location observation times and said observed environmental parameter values $pv(t=tk;n)$ ($k=1,2$) to a data receiver.

27. The method of claim 26, further comprising providing, at said location data receiver a computer that is programmed:
  to receive said at least first and second sets of location observation coordinates and said at least first and second location observation times, $t=t1$ and $t=t2$; and
  to estimate, for at least one of said location observation times, $t1$ and $t2$, and for at least one of said environmental parameter values $pv1(t;k;n)$ ($k=1, 2; n=1, \ldots, N$), a continuously variable environmental parameter field of values. $pv(x,y,z;t;k;field)$, whose value for said location observation coordinates for each of said mobile system number n ($n=1$ N), for at least one of said location observation times, $t1$ and $t2$, is equal to a corresponding environmental parameter value $pv1(t;k;n)$ at the corresponding location observation coordinates ($x_n(t), y_n(t), z_n(t)$) for at least one of said location observation times, $t1$ and $t2$.

28. The method of claim 27, wherein said computer is further programmed:
  to compare said environmental fields of parameter values $pv(x,y,z;t; field)$ for $t=t1$ and for $t=t2$ for at least one common set of location coordinates, ($x=x_c, y=y_c, z=z_c$); and
  to estimate a rate of change of said environmental parameter value $pv(x,y,z;t; field)$ at the common location coordinates ($x=x_c, y=y_c, z=z_c$) in a time interval, defined by $t1 \leq t \leq t2$.

29. The method of claim 25, further comprising providing each of at least two of said N mobile systems, numbers $n=n1$ and $n=n2$, with a mutual repulsion mechanism so that said systems n=n1 and n=n2 repel each other when a distance between the at least two systems is less than a selected threshold distance.

30. The method of claim 29, further comprising:
providing, as said mutual repulsion mechanism for said mobile system number n=n1, a first magnetic pole mechanism having a first selected number M1 of magnetic north pole sources (M1≧2), spaced apart on an exposed surface of said mobile system number n=n1, and having a magnetic south pole source, positioned at a location on said mobile system number n=n1 that is spaced apart from each of the M1 north magnetic pole sources; and
providing, as said mutual repulsion mechanism for said mobile system number n=n2, a second magnetic pole mechanism having a second selected number M2 of magnetic north pole sources (M2≧2), spaced apart on an exposed surface of said mobile system number n=n2, and having a magnetic south pole source, positioned at a location on said mobile system number n=n2 that is spaced apart from each of the M2 north magnetic pole sources,
whereby at least one of the M1 magnetic north pole sources on the mobile system number n=n1 and at least one of the M2 magnetic north pole sources on the mobile system number n=n2 will repel each other, when the at least one of the M1 magnetic north pole sources is within said threshold positive threshold distance of the at least one of the M2 magnetic north pole sources.

31. The method of claim 24, further comprising using PAM fluorometry to estimate said light intensity in said liquid at said selected location observation coordinates.

* * * * *